United States Patent
Qiu et al.

(10) Patent No.: US 10,844,000 B2
(45) Date of Patent: Nov. 24, 2020

(54) METHOD FOR PREPARING 2-FLUOROACRYLATES

(71) Applicants: LINHAI TIANYU PHARMACEUTICAL CO., LTD., Zhejiang (CN); SHANGHAI QIXUN PHARMACEUTICAL TECHNOLOGY CO., LTD., Shanghai (CN)

(72) Inventors: Kunlun Qiu, Shanghai (CN); Wenbo Wang, Shanghai (CN); Qianjie Yu, Shanghai (CN); Botao Li, Shanghai (CN); Xiongdong Lian, Shanghai (CN); Gongyong Li, Shanghai (CN)

(73) Assignees: Linhai Tianyu Pharmaceutical Co., Ltd., Zhejiang (CN); Shanghai Qixun Pharmaceutical Technology Co., Ltd., Shanghai (CN)

( * ) Notice: Subject to any disclaimer, the term of this patent is extended or adjusted under 35 U.S.C. 154(b) by 0 days.

(21) Appl. No.: 16/626,211

(22) PCT Filed: Jan. 11, 2018

(86) PCT No.: PCT/CN2018/072199
§ 371 (c)(1),
(2) Date: Dec. 23, 2019

(87) PCT Pub. No.: WO2019/000910
PCT Pub. Date: Jan. 3, 2019

(65) Prior Publication Data
US 2020/0123095 A1 Apr. 23, 2020

(30) Foreign Application Priority Data
Jun. 28, 2017 (CN) .......................... 2017 1 0505701

(51) Int. Cl.
*C07C 67/39* (2006.01)
(52) U.S. Cl.
CPC .................... *C07C 67/39* (2013.01)
(58) Field of Classification Search
CPC ...................................... C07C 67/39
See application file for complete search history.

(56) References Cited

U.S. PATENT DOCUMENTS 4,570,018 A * 2/1986 Aoki ..................... C07C 43/192
558/250
2020/0123095 A1 4/2020 Qiu et al.

FOREIGN PATENT DOCUMENTS

| CN | 102432465 | 5/2012 |
| CN | 107417524 | 12/2017 |
| WO | WO-85/03931 | 9/1985 |

OTHER PUBLICATIONS

Arbones et al., "Fluorinated Analogues of the Imidazole Insect Growth Regulator KK-42," Heterocycles (1990) 31(1):67-78.
International Search Report and Written Opinion for PCT/CN2018/072199, dated Mar. 30, 2018, 9 pages.
Jun et al., "Production Technics and Current Development of Methyl Methacrylate," Guangdong Chemical Industry (2013) vol. 40, No. 22, 3 pages.
Organo-Fluorine Industry, "Synthesis Perfonnance and Application of Fluorinated Acrylate Copolymer," (1993) No. 3, 6 pages.

* cited by examiner

Primary Examiner — Paul A Zucker
(74) Attorney, Agent, or Firm — Morrison & Foerster LLP

(57) ABSTRACT

Disclosed is a method for preparing a 2-fluoroacrylate, comprising the steps of: (1) mixing a vinyl ether having the structure of formula A with dichloromonofluoromethane to yield a substituted cyclopropane compound having the structure of formula B; (2) mixing the substituted cyclopropane compound having the structure of formula B with $R^2OH$ to yield an acetal product having the structure of formula C, followed by hydrolysis to yield 2-fluoroacrylaldehyde having the structure of formula D; or reacting the substituted cyclopropane compound having the structure of formula B with water to yield 2-fluoroacrylaldehyde having the structure of formula D via hydrolysis; (3) oxidizing 2-fluoroacrylaldehyde having the structure of formula D to yield 2-fluoroacrylic acid having the structure of formula E; and (4) mixing 2-fluoroacrylic acid having the structure of formula E with $R^3OH$ to yield a 2-fluoroacrylate having the structure of formula F.

14 Claims, No Drawings

METHOD FOR PREPARING 2-FLUOROACRYLATES

FIELD OF THE INVENTION

The present invention relates to chemical synthesis, particularly a method for producing 2-fluoroacrylates.

BACKGROUND 2-fluoroacrylates are important pharmaceutical and pesticidal intermediates. One example is Veltassa (patiromer), a high molecular polymer drug developed by Relysa US for treating hyperkalemia in CKD patients, which is produced from a 2-fluoroacrylate. At the same, 2-fluoroacrylates are essential monomers in fluorinated optical fibers. Fluorinated optical fibers have high glass transition temperatures, low surface energy and are aging resistant. 2-fluoroacrylates are also useful for producing high strength structural materials, such as those for the cockpit windshield on an aircraft and those for processing microcrystalline etched integrated circuits and electronic circuit boards.

Present processes of synthesis of 2-fluoroacrylates mainly include the followings:

Reaction of 2-fluoroacetate with formaldehyde, followed by dehydration to give the end product, wherein ethyl 2-fluoroacetate is highly toxic and the addition reaction with formaldehyde requires cryogenic-control and an alkali reagent that is fairly expensive;

Synthesis from 2-chloropropionate via fluorination, NBS bromination and elimination to give the end product, wherein stoichiometric NBS and DBU are required; and Synthesis from 2-fluoromalonate via addition with formaldehyde under a basic condition, followed by dehydration and decarboxylation to give the end product, for which the cost of raw materials is high while the atom utilization economy is low.

Accordingly, there exist the need for a method for producing 2-fluoroacrylates, which provides improved environment friendliness, product selectivity, product purity, atom economy and cost effectiveness.

SUMMARY OF THE INVENTION

An object of the invention is to provide a new method for producing 2-fluoroacrylates.

The present invention provides a method for preparing a 2-fluoroacrylate having the structure of formula F, said method comprises the steps of: (1) mixing a vinyl ether having the structure of formula A with dichloromonofluoromethane to yield a substituted cyclopropane compound having the structure of formula B;

(2) mixing the substituted cyclopropane compound having the structure of formula B with $R^2OH$ to yield an acetal product having the structure of formula C, followed by hydrolysis to yield 2-fluoroacrylaldehyde having the structure of formula D; or reacting the substituted cyclopropane compound having the structure of formula B with water to yield 2-fluoroacrylaldehyde having the structure of formula D via hydrolysis;

(3) oxidizing 2-fluoroacrylaldehyde having the structure of formula D to yield 2-fluoroacrylic acid having the structure of formula E; and (4) mixing 2-fluoroacrylic acid having the structure of formula E with $R^3OH$ to yield a 2-fluoroacrylate having the structure of formula F;

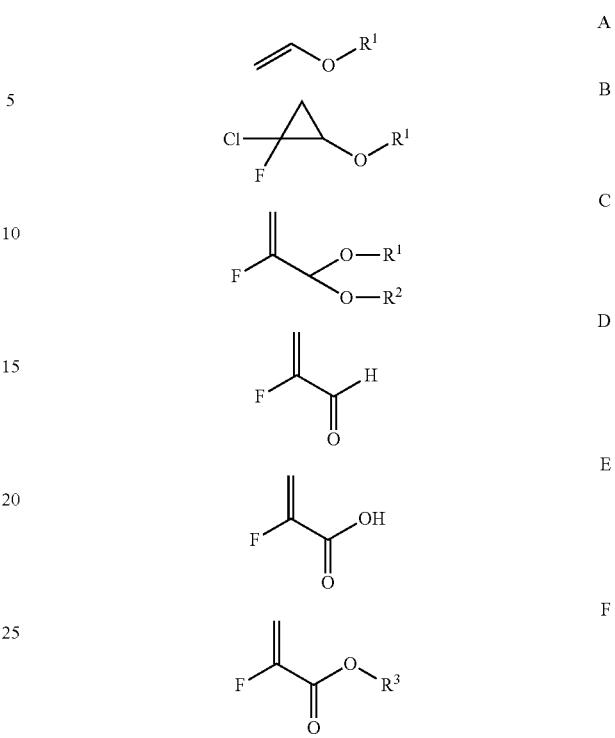

Wherein, $R^1$, $R^2$ and $R^3$ are each independently selected from the group consisting of C1 to C20 substituents of a fatty or an aromatic structure.

In a preferred embodiment, the addition reaction upon mixing in step (1) includes a phase transfer catalyst; wherein said phase transfer catalyst may be one or two or more selected from the group consisting of tetramethylammonium chloride, tetrabutylammonium chloride, tetraoctylammonium chloride, methyltrioctyl ammonium chloride, tetraoctyl ammonium bromide, tetrahexylammonium chloride, tetrabutylammonium iodide, tetrabutylammonium bromide and tri-dodecylmethylammonium iodide.

In another preferred embodiment, in step (2), the substituted cyclopropane compound having the structure of formula B is mixed with $R^2OH$ at a temperature of 80-150° C.; more preferably 80-115° C.; most preferably 110-115° C.

In another preferred embodiment, in step (2), the acetal product having the structure of formula C resulted from mixing the substituted cyclopropane compound having the structure of formula B with $R^2OH$ is hydrolyzed under an acidic condition to yield 2-fluoroacrylaldehyde having the structure of formula D.

In another preferred embodiment, said acidic condition includes a reagent selected from the group consisting of an aqueous solution of hydrochloric acid, an aqueous solution of sulfuric acid, an aqueous solution of phosphoric acid, an aqueous solution of formic acid and an aqueous solution of acetic acid, more preferably an aqueous solution of hydrochloric acid.

In another preferred embodiment, the oxidization in step (3) utilizes an oxidizing agent selected from the group consisting of sodium chlorite, sodium hypochlorite, 30% hydrogen peroxide, peracetic acid, peroxybenzoic acid, m-chloroperoxybenzoic acid, sodium persulfate, t-butanol peroxide; more preferably 30% hydrogen peroxide, peroxybenzoic acid or oxygen or air.

In another preferred embodiment, the oxidization in step (3) utilizes a catalyst selected from the group consisting of an iron salt, a vanadium salt, tungstate, a molybdenum salt or a complex salt derived therefrom; more preferably, said catalyst is selected from the group consisting of ferric chloride, ferrous sulfate, ferrous chloride, tungstic acid, sodium tungstate, ferric acetylacetonate or cobalt diacetylacetonate.

In another preferred embodiment, the mixing in step (4) is conducted at a temperature of 10-50° C.; more preferably 30-40° C.

In another preferred embodiment, R1, R2 and R3 are each independently selected from the group consisting of C1 to C10 substituents of a fatty or an aromatic structure, preferably each independently selected from the group consisting of methyl, ethyl, propyl or butyl.

Accordingly, the present invention provides a method for producing 2-fluoroacrylate with improved environment friendliness, product selectivity, product purity, atom economy and cost effectiveness.

DETAILED DESCRIPTION

The present inventors, through extensive and intensive work of exploration, find that vinyl monoethers, which are stable and easily available, can be used as the starting material to produce 2-fluoroacrylate via a process comprising cyclization, acetalization, oxidation and esterification. In such a process, the intermediates of the steps each have a good stability, which allows an effective quality control via refining of the intermediates so as to ensure a high quality for the end product. These constitute the basis of the invention.

The method for producing 2-fluoroacrylate according to the present invention comprises the steps of:

(1)

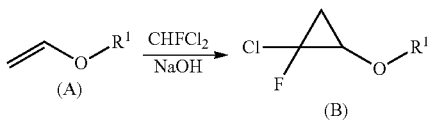

(2)

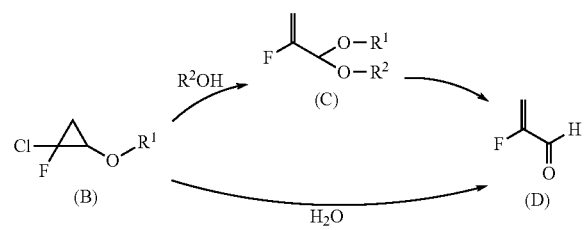

(3)

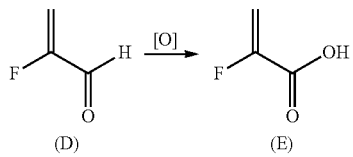

(4)

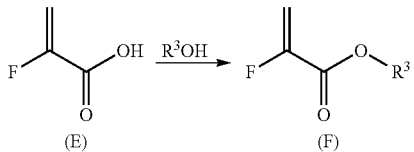

Wherein, $R^1$, $R^2$ and $R^3$ are each independently selected from the group consisting of C1 to C20 substituents of a fatty or an aromatic structure, preferably C1 to C10 substituents of a fatty or an aromatic structure, and more preferably methyl, ethyl, propyl or butyl.

Specifically,

For the first step, a vinyl ether having the structure of formula A is reacted with dichloromonofluoromethane via an addition reaction, which yields a substituted cyclopropane compound having the structure of formula B;

For the second step, the substituted cyclopropane compound having the structure of formula B is reacted with a monohydric alcohol under a basic condition to yield an acetal product having the structure of formula C, which is followed by hydrolysis under an acidic condition to yield 2-fluoroacrylaldehyde having the structure of formula D; or, the substituted cyclopropane compound having the structure of formula B is reacted with water under heating for a hydrolysis to yield 2-fluoroacrylaldehyde having the structure of formula D;

For the third step, 2-fluoroacrylaldehyde having the structure of formula D is oxidized to yield 2-fluoroacrylic acid having the structure of formula E;

For the fourth step, 2-fluoroacrylic acid having the structure of formula E is reacted with a monohydric alcohol to yield a 2-fluoroacrylate having the structure of formula F.

In the first step according to the present invention, the temperature of the addition reaction is 0-50° C., preferably 10-30° C. The addition reaction includes a vinyl ether, preferably vinyl methyl ether, vinyl ethyl ether or vinyl butyl ether, as the substrate. The addition reaction is conducted under a basic condition in the presence of an alkaline selected from the group consisting of sodium hydroxide, potassium hydroxide or lithium hydroxide, preferably sodium hydroxide. The addition reaction includes a solvent comprising an organic solvent and water, wherein the organic solvent is selected from the group consisting of methylene chloride, toluene, chlorobenzene, n-heptane, ethyl acetate or methyl tert-butyl ether. The addition reaction includes a phase transfer catalyst, which may be one or two or more selected from the group consisting of tetramethylammonium chloride, tetrabutylammonium chloride, tetraoctyl ammonium chloride, methyltrioctyl ammonium chloride, tetraoctyl ammonium bromide, tetrahexylammonium chloride, tetrabutylammonium iodide, tetrabutylammonium bromide and tri-dodecylmethylammonium iodide.

In the second step according to the present invention, the temperature of the reaction with the monohydric alcohol is 80-150° C., preferably 110-115° C. The reaction with the monohydric alcohol includes an alkaline selected from the group consisting of sodium hydroxide, potassium hydroxide, sodium carbonate, potassium carbonate, lithium hydroxide, triethylamine, tri-n-propylamine, tri-n-butylamine, diisopropylethylamine or pyridine, preferably pyridine, sodium carbonate, triethylamine, tri-n-propylamine or diisopropylethylamine.

In the above-said second step, ring-opening of the acetal intermediate having the structure of formula C and lysis in the presence of the alkaline and the alcohol under heating yields a 2-fluoroacrolein acetal. The $R^2$ of the monohydric alcohol includes but is not limited to C1 to C20 substituents of a fatty or an aromatic structure, preferably methanol, ethanol, propanol or n-butanol. The compound having the structure of formula C can be deep-purified to ensure the high quality of the final product. Methods for the purification include but are not limited to distillation.

In the above-said second step, the temperature of the hydrolysis under an acidic condition is 50-90° C., preferably 65-75° C. The said acidic condition includes a reagent selected from the group consisting of an aqueous solution of hydrochloric acid, an aqueous solution of sulfuric acid, an aqueous solution of phosphoric acid, an aqueous solution of formic acid and an aqueous solution of acetic acid, preferably an aqueous solution of hydrochloric acid.

The 2-fluoroacrylaldehyde yielded from the lysis in presence of water in the above-said second step has the structure of formula D.

In the third step according to the present invention, the temperature of the oxidization is 0-60° C., preferably 15-25° C. The oxidization utilizes a oxidizing agent selected from the group consisting of sodium chlorite, sodium hypochlorite, 30% hydrogen peroxide, peracetic acid, peroxybenzoic acid, m-chloroperoxybenzoic acid, sodium persulfate and tert-butyl peroxide, preferably 30% hydrogen peroxide, peroxybenzoic acid or oxygen or air. The oxidization may comprise a catalyst, such as an iron salt, a vanadium salt, tungstate, a molybdenum salt or a complex salt derived therefrom, including but not limited to ferric chloride, ferrous sulfate, ferrous chloride, tungstic acid, sodium tungstate, ferric acetylacetonate or cobalt diacetylacetonate. The oxidization may comprise a reaction solvent being one or two or more selected from the group consisting of toluene, methanol, ethanol, n-heptane, n-hexane and dichloromethane.

In a preferred embodiment according to the present invention, 2-fluoroacrylic acid having the structure of formula E resulted from the third step is purified via crystallization before entering the fourth step.

In the fourth step according to the present invention, the temperature in the etherification reaction is 10-50° C., preferably 30-40° C. $R^3$ of the monohydric alcohol therein includes but is not limited to C1 to C20 substituents of a fatty or an aromatic structure, preferably methanol, ethanol, propanol or n-butanol. The etherification reaction may comprise an esterifying agent, such as concentrated sulfuric acid, ion exchange resins, immobilized acid, thionyl chloride, oxalyl chloride, phosphorus oxychloride, phosgene, etc. The etherification reaction may be conducted in absence or in presence of a solvent, wherein the solvent, if present, may be for example one or two or more selected from the group consisting of toluene, n-heptane, n-hexane, dichloromethane, ethyl acetate and isopropyl acetate.

All the features said above or below in specific examples can be provided in any combinations thereof. All the features in the present disclosure can be provided in any combinations with one or more composition. Each of the features can be replaced by an alternative of an identical, equivalent or similar effect. Therefore, unless otherwise specified, each specific feature in this disclosure is just an ordinary example of its equivalent or similar counterparts.

The present invention mainly has the advantages including the following:

1. The process of production according to the present invention is easy to operate, wherein the reaction conditions are mild, and is thus feasible in the sense of an industrial scale;

2. The process of production according to the present invention starts from vinyl monoethers as the starting material, which is stable and easily available, e.g., commercially available in bulks, and the intermediates of the steps have fairly good stability; and 3. The process of production according to the present invention allows an effective quality control, wherein stable intermediates (the acetal intermediate having the structure of formula C and the solid intermediate (2-fluoroacrylic acid having the structure of formula E) are yielded, so as to ensure a high quality for the end product (a 2-fluoroacrylate having the structure of formula F).

The present invention will be further described below by referring to the specific embodiments. It should be understood that these examples are only provided for the purpose of illustration, without intending to limit the scope of the invention in any sense. In the following examples, experiments with no conditions given particularly were conducted under the conditions according to general practices or manufacturer's instructions. Unless otherwise specified, all percentages, ratios, proportions or parts are by weight. Herein, percent by weight/volume is expressed in the unit as commonly known and refers to, for instance, the amount of a solute by weight in a volume of 100 ml of solution. Unless otherwise defined, all the professional and scientific terms used herein have the meanings commonly known by those skilled in the art. In addition, any methods and materials similar or equivalent to those as described are also useful in the present invention method. The preferred embodiments and materials described herein are merely for the purpose of illustration.

EXAMPLE 1

Preparation of 2-butoxy-1-chloro-1-fluorocyclopropane

Into a 500 ml four-necked flask, water 42.8 g (2.38 mol), sodium hydroxide 42.8 g (1.07 mol), vinyl butyl ether 20 g (0.2 mol) and toluene 49.2 g (0.58 mol) were added in the specified order under nitrogen protection. At the elevated temperature of 40° C., dichloromonofluoromethane 27.79 g (0.27 mol) was added dropwise, and the mixture was reacted for 12 h at the maintained temperature. Layers are separated, the organic phase was distilled under reduced pressure, solvent being recovered, and further distillation at raised temperature gave the product of 2-butoxy-1-chloro-1-fluorocyclopropane. Purity: 98%, Yield: 96%.

$^1$H NMR (400 MHz, CDCl$_3$): 3.74-3.39 (m, 3H), 1.75-1.49 (m, 3H), 1.49-1.22 (m, 3H), 1.04-0.82 (m, 3H).

$^{19}$F NMR (400 MHz, CDCl$_3$): −158.76--−159.38 (m, 1F) (43%, trans-isomer), −137.11--−138.48 (m, 1F) (57%, cis-isomer).

EXAMPLE 2

Preparation of 1-((1-butoxy-2-fluoropropenyl)oxy)butane

Into a 250 ml four-necked flask, pyridine 15.3 g (0.19 mol), n-butanol 15.5 g (0.21 mol), 2-butoxy-1-chloro-1-fluorocyclopropane 30.0 g (0.18 mol) were added and reacted for 16 h under reflux. 1-((1-butoxy-2-fluoropropenyl)oxy)butane was obtained from distillation. Yield: 98%.

$^1$H NMR (400 MHz, CDCl$_3$): 1.00-0.69 (m, 6H), 1.42-1.20 (m, 4H), 1.62-1.42 (m, 4H), 3.68-3.22 (m, 4H), 4.79-4.55 (m, 2H), 4.90-4.79 (s, 1H).

$^{19}$F NMR (400 MHz, CDCl$_3$): −137.46--−138.52 (m, 1F).

EXAMPLE 3

Preparation of 2-fluoroacrylaldehyde

To 1-((1-butoxy-2-fluoropropenyl)oxy)butane, 10% HCl 73 g (0.2 mol) was added dropwise, and reacted at 70° C. for 2 hours, which was followed by rectification to give the product of 2-fluoroacrylaldehyde. Yield: 90%.

$^1$H NMR (400 MHz, CDCl$_3$): 5.63-5.38 (m, 1H), 5.87-5.65 (m, 1H), 9.47-9.03 (d, 1H).

$^{19}$F NMR (400 MHz, CDCl$_3$): −121.28-−125.09 (m, 1F).

EXAMPLE 4

Preparation of 2-fluoroacrylaldehyde 1-((1-butoxy-2-fluoropropenyl)oxy)butane was mixed with steam at 1:1 and, with nitrogen as the carrier gas, went through the cracker at 250° C. Then, the exhaust gas was cooled down, rectification of the mixture gave the product of 2-fluoroacrylaldehyde. Yield: 70%.

$^1$H NMR (400 MHz, CDCl$_3$): 5.63-5.38 (m, 1H), 5.87-5.65 (m, 1H), 9.47-9.03 (d, 1H).

$^{19}$F NMR (400 MHz, CDCl$_3$): −121.28-−125.09 (m, 1F).

EXAMPLE 5

Preparation of 2-fluoroacrylic acid

In a 250 ml four-necked flask, 2-fluoroacrylaldehyde 8.89 g (0.12 mol) was mixed with ferric trichloride 0.89 g (5.5 mmol), at the maintained temperature of 30° C. 30% hydrogen peroxide 40.8 g (0.36 mol) was added dropwise, stirred for 2 h at the maintained temperature. Extraction was conducted by adding ethyl acetate 20 g. The organic phase was washed with water and concentrated to dry, which gave a crude product of 2-fluoroacrylic acid. Then crystallization using 10 g n-heptane gave the final product of 2-fluoroacrylic acid. Yield: 90%.

$^1$H NMR (400 MHz, CDCl$_3$): 5.62-5.17 (m, 1H), 6.07-5.62 (m, 1H), 7.45-7.20 (s, 1H).

$^{19}$F NMR (400 MHz, CDCl$^3$): −118.55 (dd, 1F).

EXAMPLE 6

Preparation of 2-fluoroacrylic acid

In a 250 ml four-necked flask, 2-fluoroacrylaldehyde 8.89 g (0.12 mol), m-cpba 26 g (0.15 mol) and dichloromethane 30 g were mixed and reacted at 20° C. under stirring for 2 h. Then the mixture was cooled down to about 0° C. and filtered. The filtrate was concentrated to dry, which gave a crude product of 2-fluoroacrylic acid. Crystallization using 10 g n-heptane gave the final product of 2-fluoroacrylic acid. Yield: 92%.

$^1$H NMR (400 MHz, CDCl$_3$): 5.62-5.17 (m, 1H), 6.07-5.62 (m, 1H), 7.45-7.20 (s, 1H).

$^{19}$F NMR (400 MHz, CDCl$_3$): −118.55 (dd, 1F).

EXAMPLE 7

Preparation of methyl 2-fluoroacrylate

In a 100 ml three-necked flask, methanol 6.4 g (0.2 mol) was mixed with 2-fluoroacrylic acid 8.64 g (0.096 mol). The temperature was raised to 30° C., and concentrated sulphuric acid 4.9 g (0.05 mol) was added dropwise. The reaction was maintained at 30-35° C. for 2 h. Saturated NaHCO$_3$ was added to neutralize the system to a neutral pH. Extraction was conducted by adding methyl tert-butyl ether 20 g (0.23 mol). The organic phase was rectified to give the product of methyl 2-fluoroacrylate. Yield: 89%.

$^1$H NMR (400 MHz, CDCl$_3$): 3.89-3.78 (s, 3H), 5.35-5.25 (m, 1H), 5.74-5.55 (m, 1H).

$^{19}$F NMR (400 MHz, CDCl$_3$): −117.72 (dd, 1F).

EXAMPLE 8

Preparation of methyl 2-fluoroacrylate

In a 100 ml three-necked flask, at 5-10° C., 2-fluoroacrylic acid 8.64 g (0.096 mol) was mixed with thionyl chloride 13.1 g (0.11 mol). The temperature was raised to 30° C., and methanol 6.4 g (0.2 mol) was added dropwise. The reaction was maintained at 30-35° C. for 2 h. Saturated NaHCO$_3$ was added to neutralize the system to neutral pH. Extraction was conducted by adding methyl tert-butyl ether 20 g (0.23 mol). The organic phase was rectified to give the product of methyl 2-fluoroacrylate. Yield: 93%.

$^1$H NMR (400 MHz, CDCl$_3$): 3.89-3.78 (s, 3H), 5.35-5.25 (m, 1H), 5.74-5.55 (m, 1H)

$^{19}$F NMR (400 MHz, CDCl$_3$): −117.72 (dd, 1F).

Quality metrics of the methyl 2-fluoroacrylate products from Examples 7 and 8

|  | Method of observation | Result |
| --- | --- | --- |
| Appearance | Visual | colorless to light yellow transparent liquid |
| Purity | GC-FID | >99.5% |
| Water Content | KF | <500 ppm |
| R21 | GC-FID | ND. |
| Methyl 2-chloroacrylate | GC-FID | <1 ppm |
| Methyl 2-bromoacrylate | GC-FID | ND. |
| Methane chloride | GC-FID | ND. |
| Methyl 2-fluoroacetate | GC-FID | ND. |

EXAMPLE 9

Preparation of butyl 2-fluoroacrylate

In a 100 ml three-necked flask, butanol 14.8 g (0.2 mol) was mixed with 2-fluoroacrylic acid 8.64 g (0.096 mol). The temperature was raised to 30° C., and concentrated sulphuric acid 4.9 g (0.05 mol) was added dropwise. The reaction was maintained at 30-35° C. for 2 h. Saturated NaHCO$_3$ was added to neutralize the system to neutral pH. Extraction was conducted by adding methyl tert-butyl ether 20 g (0.23 mol). The organic phase was rectified to give the product of butyl 2-fluoroacrylate. Yield: 90%.

$^1$H NMR (400 MHz, CDCl$_3$): 1.03-0.81 (t, 3H), 1.50-1.30 (m, 2H), 1.78-1.60 (m, 2H), 4.34-4.10 (m, 2H), 5.90-5.18 (m, 2H).

$^{19}$F NMR (400 MHz, CDCl$_3$): −117.52 (dd, 1F).

Quality metrics of the butyl 2-fluoroacrylate product from EXAMPLE 9

|  | Method of observation | Result |
| --- | --- | --- |
| Appearance | Visual | colorless to light yellow transparent liquid |
| Purity | GC-FID | >99.5% |
| Water Content | KF | <500 ppm |
| R21 | GC-FID | ND. |
| Butyl 2-chloroacrylate | GC-FID | <1 ppm |
| Butyl 2-bromoacrylate | GC-FID | ND. |
| Methane chloride | GC-FID | ND. |
| Butyl 2-fluoroacetate | GC-FID | ND. |

Described above are just preferred embodiments of the present invention, which were provided with no intention to limit the scope of the present invention in technique. The scope of the invention in technique in defined in a broad sense by the claims of the application. Any technical entity or method, which is the same as or an equivalent variation of a claim of the invention, is deemed as being included in the scope of the claim.

The invention claimed is:

1. A method for producing a 2-fluoroacrylate having the structure of formula F, wherein, said method comprises the steps of: (1) mixing a vinyl ether having the structure of formula A with dichloromonofluoromethane to yield a substituted cyclopropane compound having the structure of formula B;

(2) mixing the substituted cyclopropane compound having the structure of formula B with $R^2OH$ to yield an acetal product having the structure of formula C, followed by hydrolysis to yield 2-fluoroacrylaldehyde having the structure of formula D, wherein the substituted cyclopropane compound having the structure of formula B is mixed with $R^2OH$ at a temperature of 80-150° C.; or reacting the substituted cyclopropane compound having the structure of formula B with water to yield 2-fluoroacrylaldehyde having the structure of formula D via hydrolysis;

(3) oxidizing 2-fluoroacrylaldehyde having the structure of formula D to yield 2-fluoroacrylic acid having the structure of formula E, wherein the oxidization in step (3) utilizes a catalyst selected from the group consisting of an iron salt, a vanadium salt, tungstate, a cobalt salt, a molybdenum salt and a complex salt derived therefrom, and is conducted at a temperature of 0-60° C.;

(4) mixing 2-fluoroacrylic acid having the structure of formula E with $R^3OH$ to yield a 2-fluoroacrylate having the structure of formula F, wherein the 2-fluoroacrylic acid having the structure of formula E is mixed with $R^3OH$ at a temperature of 10-50° C.;

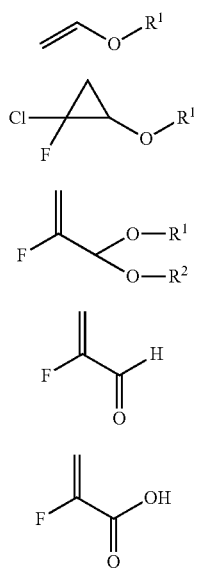

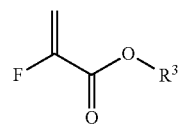

wherein, each of $R^1$, $R^2$ and $R^3$ is independently a C1 to C20 fatty or aromatic substituent.

2. The method according to claim 1, wherein, the addition reaction upon mixing in step (1) includes a phase transfer catalyst; wherein said phase transfer catalyst is one or two or more selected from the group consisting of tetramethylammonium chloride, tetrabutylammonium chloride, tetraoctyl ammonium chloride, methyltrioctyl ammonium chloride, tetraoctyl ammonium bromide, tetrahexylammonium chloride, tetrabutylammonium iodide, tetrabutylammonium bromide and tri-dodecylmethylammonium iodide.

3. The method according to claim 1, wherein, in step (2), the substituted cyclopropane compound having the structure of formula B is mixed with $R^2OH$ at a temperature of 80-115° C.

4. The method according to claim 1, wherein, in step (2), the substituted cyclopropane compound having the structure of formula B is mixed with $R^2OH$ at a temperature of 110-115° C.

5. The method according to claim 1, wherein, in step (2), the acetal product having the structure of formula C resulted from mixing the substituted cyclopropane compound having the structure of formula B with $R^2OH$ is hydrolyzed under an acidic condition to yield 2-fluoroacrylaldehyde having the structure of formula D.

6. The method according to claim 5, wherein, said acidic condition comprises a reagent selected from the group consisting of an aqueous solution of hydrochloric acid, an aqueous solution of sulfuric acid, an aqueous solution of phosphoric acid, an aqueous solution of formic acid and an aqueous solution of acetic acid.

7. The method according to claim 1, wherein, the oxidization in step (3) utilizes an oxidizing agent selected from the group consisting of sodium chlorite, sodium hypochlorite, 30% hydrogen peroxide, peracetic acid, peroxybenzoic acid, m-chloroperoxybenzoic acid, sodium persulfate, t-butanol peroxide, oxygen, and air.

8. The method according to claim 1, wherein, the oxidization in step (3) utilizes a catalyst selected from the group consisting of an iron salt, a vanadium salt, tungstate, a molybdenum salt and a complex salt derived therefrom.

9. The method according to claim 1, wherein, said catalyst is selected from the group consisting of ferric chloride, ferrous sulfate, ferrous chloride, tungstic acid, sodium tungstate, ferric acetylacetonate and cobalt diacetylacetonate.

10. The method according to claim 1, wherein, the mixing in step (4) is conducted at a temperature of 30-40° C.

11. The method according to claim 1, wherein, each of $R^1$, $R^2$ and $R^3$ is independently a C1 to C10 fatty or aromatic substituent.

12. The method according to claim 6, wherein the agent is an aqueous solution of hydrochloric acid.

13. The method according to claim 7, wherein the oxidizing agent is selected from the group consisting of 30% hydrogen peroxide, peroxybenzoic acid, oxygen, and air.

14. The method according to claim 11, wherein each of $R^1$, $R^2$ and $R^3$ is independently selected from the group consisting of methyl, ethyl, propyl, and butyl.

* * * * *